United States Patent [19]

Karabinos et al.

[11] 4,250,319
[45] Feb. 10, 1981

[54] DERIVATIVES OF THIOPHENE

[75] Inventors: Joseph V. Karabinos, Orange, Conn.; Louis G. Nickell, Honolulu, Hi.

[73] Assignee: W. R. Grace & Co., New York, N.Y.

[21] Appl. No.: 760,825

[22] Filed: Jan. 21, 1977

Related U.S. Application Data

[62] Division of Ser. No. 589,401, Jun. 23, 1975, Pat. No. 4,013,681.

[51] Int. Cl.$^3$ .................. C07D 333/24; A01N 43/07
[52] U.S. Cl. ...................... 549/61; 549/69; 549/71; 71/90
[58] Field of Search ............... 260/332.2 R, 332.2 A, 260/332.2 C, 332.5, 329 S, 329 AM; 549/61, 69, 71

[56] References Cited

U.S. PATENT DOCUMENTS 3,705,910   12/1972   Lundberg et al. ............. 260/329 S
4,021,224   5/1977    Pallos et al. ................. 260/332.2 R

OTHER PUBLICATIONS

Sauter, "Monatsheft für Chemie", 101, 535–543 (1970).
Chem. Ber. 101, 1933–1939 (1968).

Primary Examiner—Alan Siegel
Attorney, Agent, or Firm—Burns, Doane, Swecker & Mathis

[57] ABSTRACT

New dicyclic thiophene compounds having the structural formula

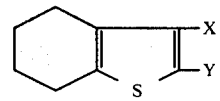

wherein X is an ester or cyano group and Y is a substituted amino group. The compounds are useful as agricultural chemicals and particularly as ripeners for sugarcane.

8 Claims, No Drawings

DERIVATIVES OF THIOPHENE

CROSS REFERENCE TO RELATED APPLICATION

This application is a division of application Ser. No. 589,401 filed June 23, 1975, now U.S. Pat. No. 4,013,681.

The use of this kind of compounds as ripeners for sugarcane is claimed in U.S. Pat. No. 3,989,505, also filed June 23, 1975.

FIELD OF THE INVENTION

This invention relates to derivatives of 2-aminotetramethylenethiophenes which are useful as agricultural chemicals.

More particularly, the invention relates to compounds having the formula

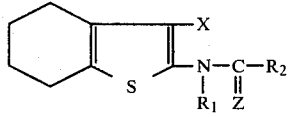

wherein X is cyano or carboalkoxy, $R_1$ is hydrogen or methyl, Z is oxygen or sulfur, and $R_2$ is a lower alkyl, chloroalkyl, or a substituted phenylamino radical.

These compounds can be prepared using 2-amino-3-cyano-4,5-tetramethylene, which has previously been described in the literature, as a starting material.

THE PRIOR ART

A number of condensed thiophene derivatives have previously been prepared and proposed by prior workers as being useful as dyes or dye intermediates (see, for instance, U.S. Pat. No. 3,555,016), as herbicides (see, for instance, U.S. Pat. Nos. 2,634,200; 3,705,910 and 3,823,161) or as pharmaceutical agents (see, for instance, U.S. Pat. No. 3,758,476).

Various methods of chemical synthesis used in preparing such compounds are described in these patents as well as elsewhere in the literature. For instance, the preparation of 2-amino-3-cyanotetramethylenethiophene, which is the basic starting material used in the present invention, has been previously described by K. Gewald in Z. Chem. 2, 305 (1962); Angew. Chem. 73, 114 (1961). Other references which describe the preparation and reactions of various condensed thiophene derivatives include K. Gewald, Ber. 98, 3571 (1965); E. C. Taylor et al, Angew. Chem. 78, 144 (1966); Int. Ed. (English) 5, 131 (1966); K. Gewald et al, Ber. 99, 94 (1966); A. M. Chacko, Ph. Dissert., Univ. of North Carolina 1965, microfilm 65-14320 Ann Arbor, Michigan; and V. P. Arya, Indian Journal of Chem. 10, 1141 (1972).

SUMMARY OF THE INVENTION

The present invention provides a certain new class of derivatives of 2-amino-3-cyano-4,5-tetramethylenethiophene which have been found to be surprisingly effective as ripeners for sugarcane and may find other uses as agricultural chemicals or chemical intermediates.

More specifically, the condensed thiophene derivatives of this invention have a general structural formula as follows:

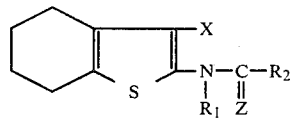

wherein X is cyano or a $C_1$-$C_4$ carboalkoxy group, e.g., carbomethoxy, carboethoxy or carbobutoxy, $R_1$ is hydrogen or methyl, Z is oxygen or sulfur, and $R_2$ is a $C_2$-$C_4$ alkyl optionally substituted by chlorine, bromine or fluorine, e.g., ethyl, butyl, 2-chloroethyl or 3-chloropropyl; or a $C_1$-$C_4$ alkyl, $C_1$-$C_4$ alkoxy, halogen or $C_1$-$C_4$ haloalkyl substituted phenylamino group, e.g.,

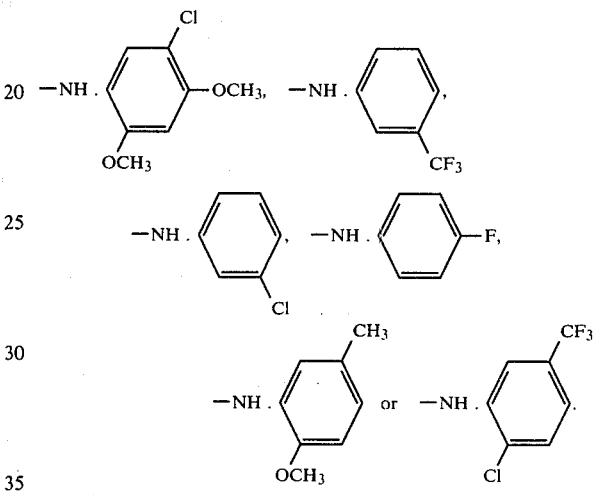

Specific examples of compounds included in the scope of this invention are:
2-trichloroacetamido-3-cyano-4,5-tetramethylenethiophene
2-propionamido-3-cyano-4,5-tetramethylenethiophene
2-(3-chloropropionamido)-3-cyano-4,5-tetramethylenethiophene
2-butyramido-3-cyano-4,5-tetramethylenethiophene
2-benzamido-3-cyano-4,5-tetramethylenethiophene
2-propionamido-3-carboethoxy-4,5-tetramethylenethiophene
2-(3-chloropropionamido)-3-carboethoxy-4,5-tetramethylenethiophene
2-butyramido-3-carboethoxy-4,5-tetramethylenethiophene
2-benzamido-3-carboethoxy-4,5-tetramethylenethiophene
2-butylureido-3-cyano-4,5-tetramethylenethiophene
2-phenylureido-3-cyano-4,5-tetramethylenethiophene
2-(5-chloro-2,4-dimethoxyphenyl)-thioureido-3-cyano-4,5-tetramethylenethiophene
2-(3-chlorophenyl)-thioureido-3-cyano-4,5-tetramethylenethiophene
2-(4-fluorophenyl)-ureido-3-cyano-4,5-tetramethylenethiophene
2-butylureido-3-carboethoxy-4,5-tetramethylenethiophene
2-phenylureido-3-carboethoxy-4,5-tetramethylenethiophene
2-(3-chlorophenyl)-ureido-3-carboethoxy-4,5-tetramethylenethiophene 2-(4-fluorophenyl)-ureido-3-carboethoxy-4,5-tetramethylenethiophene 2-(2-methoxy-5-methylphenyl)-ureido-3-carboethoxy-4,5-tetramethylenethiophene 2-(2-chloro-5-trifluoromethylphenyl)-ureido-3-carboethoxy-4,5-tetramethylenethiophene 2-(3-trifluoromethylphenyl)-ureido-3-carboethoxy-4,5-tetramethylenethiophene The thioureido derivatives, i.e., derivatives of some of the isothiocyanates, which have been preliminarily tested to date have tended to be less active than analogous compounds of the other types listed above. Nevertheless, some of the thioureido derivatives have shown themselves to be excellent ripeners for sugarcane and may have valuable properties for other agricultural uses.

2-amino-3-cyano-4,5-tetramethylenethiophene, m.p. 147°–8° C., which is the principal starting material in this invention and which is hereinafter referred to as compound (I), is prepared as described in the literature using cyclohexanone, malononitrile, an amine such as triethylamine and sulfur by the following series of reactions:

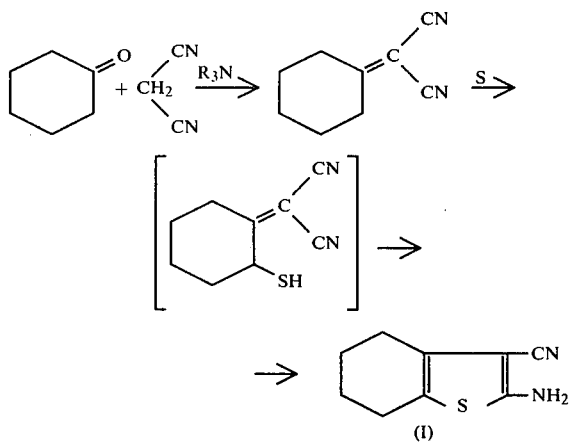

In accordance with otherwise well-known methods, the cyano group of compound (I) can be readily converted to a carboalkoxy group by reaction with a suitable alcohol under esterification conditions, e.g., by refluxing in absolute ethanol with HCl catalyst. In this manner, 2-amino-3-carboethoxy-4,5-tetramethylenethiophene is produced. This compound (II) has a melting point of 99°–101° C. and is another important starting material used in this invention.

DESCRIPTION OF SPECIFIC EMBODIMENTS

Example 1

(A) Preparation of 2-Propionamido-3-Cyano-4,5-Tetramethylenethiophene: Compound (XX)

17.8 g of compound (I) is dissolved in 100 ml acetone containing 8 g pyridine. To this solution is added 13 g propionic anhydride. The mixture is gently warmed to obtain solution and allowed to stand overnight. It is then poured into an excess of ice water and the resulting crystalline solid is recovered by filtration, and is dried and weighed 17 gm of crystalline white product, compound (XX), is recovered, m.p. 138°–140° C.

With reference to the general formula shown earlier herein, in the case of compound (XX) X is cyano, $R_1$ is hydrogen, Z is oxygen and $R_2$ is ethyl.

(B) Use of Compound (XX) as Ripener

To evaluate the efficacy of compound (XX) as a ripener for sugarcane, a treating composition is prepared by weighing out 1 gram of this compound and dispersing it in approximately 6 ml water. This mixture is diluted with water to exactly 8 ml, 1 drop of commercial Tergitol NPX (liquid) surfactant is added to the diluted mixture and the mixture is agitated by shaking prior to application.

A 0.3 ml dose of the aqueous mixture containing 38 mg compound (XX), prepared as described above, is applied on the spindle area at the top of the last visible dewlap of each of 20 stalks of sugarcane in a test plot in a commercial cane field in Hawaii, using a syringe with a fine needle as a microapplicator.

Other groups of 20 stalks each in the same test plot are treated in an identical manner for comparative purposes with "Trysban" (dimethylamine salt of 2,3,6-trichlorobenzoic acid), used as a standard because of its known and consistent good activity.

The age of the cane at the time of application was 18.5 months.

A set of 10 of these treated stalks from each group is harvested 5 weeks after such treatment and a set of 10 untreated stalks from the same plot is also harvested at the same time as a control.

The top 15 joints of each 10-stalk set of the treated stalks, as well as those of untreated control stalks from the same test plot, are removed, and each set is combined and analyzed in terms of juice purity and pol percent cane, following the so-called "press method" developed by T. Tanimoto, Hawaiian Planters' Record, 57, 133 (1964). "Pol percent cane" is a polarimetric determination and equals the percentage of sucrose if sucrose is the only optically active substance in the solution. In any event, determination of the pol percent cane is a standard and effective method for determining the sucrose content of sugarcane. The test data are given in Table I-A.

The data show that treatment with 2-propionamido-3-cyano-4,5-tetramethylenethiophene brings about a major increase in sucrose yield as compared with the untreated cane, and that this compound is actually a more effective ripener than the standard ripener, Trysben, under the conditions of this test.

TABLE I-A

| Cane Variety: 59-3775, Field 19 | | |
|---|---|---|
| Age: 18.5 months | | |
| Date of Treatment: December 19, Year Y | | |
| | Harvest Time 5 Weeks After Treatment | |
| Ripening Agent | Juice Purity | Pol % Cane |
| Compound (XX)*, 38 mg/stalk | 77.42 | 9.83 |
| Trysben (standard) | 75.45 | 9.17 |
| Control (untreated) | 69.86 | 7.18 |

*2-Propionamido-3-Cyano-4,5-Tetramethylenethiophene.

EXAMPLE 2

Preparation of 2-(3-Chloropropionamido)-3-Cyano-4,5-Tetramethylenethiophene: Compound (IV)

12 g of compound (I) is dissolved in 100 ml acetone containing 6 ml pyridine. To this solution is added 9.4 g 3-chloropropionyl chloride. The mixture is gently warmed to obtain solution, allowed to stand overnight and then poured into an excess of ice water. The resulting crystalline solid is recovered by filtration, and is dried and weighed. 17 g of compound (IV) is recovered as a tan solid which has a melting point of 162°–165° C.

With reference to the general formula shown earlier herein, in the case of compound (IV) X is cyano, $R_1$ is hydrogen, Z is oxygen and $R_2$ is 2-chloroethyl.

Compound (IV) can be used as a sugarcane ripener in the same manner as described in Example 1.

EXAMPLE 3

Preparation of 2-(5-Chloro-2,4-Dimethoxyphenyl)-Thioureido-3-Cyano-4,5-Tetramethylenethiophene: Compound (V)

8.9 g of compound (I) is dissolved in 150 ml acetone. To this solution is added 11.45 g 5-chloro-2,4-dimethoxyphenylisothiocyanate, the solution is heated to reflux and then cooled, resulting in the formation of a white crystalline compound. 19 g of this crystalline compound, compound (V), is recovered by filtration and drying. The product has a melting point of 92°–5° C.

With reference to the general formula shown earlier herein, in the case of compound (V) X is cyano, $R_1$ is hydrogen, Z is sulfur and $R_2$ is (5-chloro-2,4-dimethoxyphenyl)amino.

Compound (V), when tested as described in Example 1, shows excellent efficacy as a sugarcane ripener, being somewhat less effective than Trysben when the cane is harvested four weeks after application and somewhat more effective than Trysben when the cane is harvested five weeks after application. The results are shown in Table I-B.

TABLE I-B

Cane Variety: 59-3775, Field 48
Age: 23 months
Date of Treatment: August 7, Year Y
Dates of Harvest: September 3 and September 10, Year Y

| | Harvest Time After Treatment | | | |
|---|---|---|---|---|
| | 4 Weeks | | 5 Weeks | |
| Ripening Agent | Juice Purity | Pol % Cane | Juice Purity | Pol % Cane |
| Compound (V), 38 mg/stalk | 64.48 | 11.09 | 74.45 | 9.52 |
| Trysben (standard) | 72.73 | 11.93 | 74.01 | 9.14 |
| Control (untreated) | 63.98 | 9.57 | 68.25 | 7.85 |

EXAMPLE 4

Preparation of 2-(2-Chloroacetamido)-3-Carboethoxy-4,5-Tetramethylenethiophene: Compound (VI)

This compound, having the formula

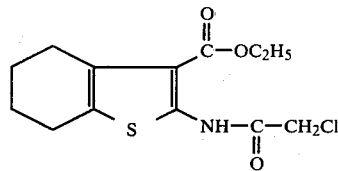

was prepared starting from compound (II) and chloroacetylchloride in acetone, using the conditions described in Example 2 in 0.1 M quantity.

With reference to the general formula, in the case of compound (VI) X is carboethoxy, $R_1$ is hydrogen, Z is oxygen and $R_2$ is chloromethyl.

The yield of compound (VI) recovered was 23 g; its melting point is 102°–5° C.

Compound (VI) can be used as a sugarcane ripener in the same manner as described in Example 1. Relevant preliminary test data are shown in Table I-C, below.

EXAMPLE 5

Preparation of 2-(3-chlorophenyl)-Ureido-3-Carboethoxy-4,5-Tetramethylenethiophene: Compound (VII)

This compound was prepared from compound (II) and m-chlorophenylisocyanate in acetone, using the conditions described in connection with the preparation of compound (V) in Example 3. Using the reactants in 0.067 M quantity, compound (VII) was recovered in a yield of 15 g. Its melting point is 162°–4° C.

Referring to the general formula, in the case of compound (VII) X is carboethoxy, $R_1$ is hydrogen, Z is oxygen and $R_2$ is 3-chlorophenylamino.

In the single screening test performed to date with this compound as a ripener for sugarcane, no significant activity was detected.

EXAMPLE 6

Preparation of 2-(4-Fluorophenyl)-Ureido-3-Carboethoxy-4,5-Tetramethylenethiophene: Compound (VIII)

This compound was prepared from compound (II) and o-fluorophenylisocyanate in acetone in 0.05 M quantity, using the procedure described in Example 3. Compound (VIII) has a melting point of 186°–8° C.

Referring to the general formula, in the case of compound (VIII) X is carboethoxy, $R_1$ is hydrogen, Z is oxygen and $R_2$ is 4-fluorophenylamino.

Relevant preliminary test data illustrating the usefulness of this compound as a ripener for sugarcane are included in Table I-C, below.

EXAMPLE 7

Preparation of 2-(2-Methoxy-5-Methylphenyl)-Ureido-3-Carboethoxy-4,5-Tetramethylenethiophene: Compound (IX)

This compound was prepared from compound (II) and 2-methoxy-5-methylphenylisocyanate in acetone, using the procedure described in Example 3. Compound (IX) has a melting point of 138°–41° C.

Relevant preliminary test data illustrating the usefulness of this compound as a ripener for sugarcane are included in Table I-C, below. As shown therein, compound (IX) shows a significant improvement in sugar yield when the treated cane is harvested four weeks after treatment. When harvested five weeks from the date of treatment, no significant increase in sugar yield is obtained in comparison with untreated cane of the same age. This illustrates that some ripeners are useful in increasing the yield of sucrose when the need for a relatively early harvest date is anticipated, though the same ripeners give no appreciable advantage over untreated cane if the cane can be allowed more time for natural maturation.

EXAMPLE 8

Preparation of 2-(2-Chloro-5-Trifluoromethylphenyl)-Ureido-3-Carboethoxy-4,5-Tetramethylenethiophene: Compound (X)

This compound was prepared from compound (II) and 2-chloro-5-trifluoromethylphenylisocyanate in acetone, using the procedure described in Example 3.

Compound (X) has a melting point of 187°–9° C.

Relevant preliminary test data illustrating the usefulness of this compound as a ripener for sugarcane are also included in Table I-C, below. As in the case of compound (IX), compound (X) shows very significant ripening activity in the case of the cane sample which was harvested four weeks after treatment while no significant advantage over untreated cane of the same age is obtained in the case of the cane sample which was harvested five weeks after treatment.

Of course, those skilled in the art will understand that optimum ripener activity varies from compound to compound and may occur from three to over thirteen weeks after application. Moreover, some compounds show a broad plateau of maximum activity, a highly desirable characteristic, while other compounds exhibit sharper peak. Specific dosage understandably also can have a significant effect on the magnitude of maximum activity as well as the relationship between activity and time after application. The effect of a particular ripener also varies to some extent with cane variety, its age at the time of application as well as the specific dosage applied. When substantially more than optimum dosage is applied, it may cause too rapid drying of the cane and have an adverse effect on sucrose production. For all these reasons, it is generally advisable to determine by preliminary empirical tests the optimum conditions for use of any given compound under any particular conditions.

TABLE I-C

| Cane Variety: | 59-3775, Field 19 | | | |
| Age: | 20.75 months | | | |
| Date of Treatment: | February 28, Year Y + 1 | | | |
| Dates of Harvest: | March 27 and April 4, Year Y + 1 | | | |
| Dosage of Ripener: | 39 mg per stalk | | | |

| | 4 Weeks | | 5 Weeks | |
| --- | --- | --- | --- | --- |
| Compound | Juice Purity | Pol % Cane | Juice Purity | Pol % Cane |
| VI | 81.75 | 10.35 | 84.72 | 12.18 |
| VII | 77.07 | 9.68 | 81.29 | 10.85 |
| VIII | 80.91 | 10.87 | 83.60 | 11.69 |
| IX | 81.33 | 10.38 | 77.17 | 9.60 |
| X | 82.33 | 10.71 | 81.30 | 10.65 |
| Trybsen (standard) | 78.77 | 10.32 | 83.76 | 11.75 |
| Control (untreated) | 78.47 | 9.42 | 81.48 | 10.27 |

Compound VI was prepared as described in Example 4.
Compound VII was prepared as described in Example 5.
Compound VIII was prepared as described in Example 6.
Compound IX was prepared as described in Example 7.
Compound X was prepared as described in Example 8.

Other compounds which have been prepared following the general procedures set forth above and which are useful as ripeners for sugarcane are described in Examples 9 and 10.

EXAMPLE 9

2-Propionamido-3-Carboethoxy-4,5-Tetramwethylenethiophene: Compound (XIII)

Starting materials: Compound (II) and propionic anhydride.

Method of synthesis was the same as in Example 1. The product has a melting point of 61°–4° C.

EXAMPLE 10

2-(3-Trifluoromethylphenyl)-Ureido-3-Carboethoxy-4,5-Tetramethylenethiophene: Compound (XIV)

Starting materials: Compound (II) and m-trifluoromethylphenylisocyanate.

Method of synthesis used was the same as in Example 3. The product has a melting point of 176°–8° C.

The condensed thiophene compounds of this invention may be used for increasing the sucrose yield of sugarcane by applying a spray or dust comprising one or more of such compounds to maturing sugarcane stalks in a crop near the end of its normal maturation cycle, and harvesting such a crop some weeks later. The composition is applied directly to the stalks by spraying, dusting or the like in order that it be deposited on the stalks including the younger, growing parts thereof. The normal maturation cycle of sugarcane under conditions such as those prevailing in Hawaii is from about 18 to about 36 months, though in some areas sugarcane is ripe and ready for harvest in 9 to 12 months.

The preferred usage form is a mixture containing one or more of the condensed thiophene compounds in an aqueous solution or suspension utilizing one or a combination of known surface active agents commonly and variously used in the prior art as wetting agents, detergents or emulsifying agents. However, dry dusting compositions containing the condensed thiophene compound or compounds and a solid diluent such as clay are also useful. It is recommended that the treating mixtures embodying the present invention be applied to the cane crop about two to ten weeks prior to harvest, preferably between about four and ten weeks prior to harvest.

Good results are obtained when the cane crop is treated in the field at a rate in the range of from 1 to 4 pounds per acre (about 1 to 4 kg/hectare) of the active condensed thiophene compound. However, higher rates, e.g., up to about 30 pounds per acre (about 30 kg/hectare), or rates lower than 1 pound per acre (about 1 kg/hectare) of the chemical ripener can also be used. The optimum amount will vary somewhat depending on the particular compound used, its mode of application, environmental conditions, time of year, and age and variety of cane being treated, but can be readily determined for each particular case by preliminary testing.

When the active agent is applied in the field in the form of an aqueous solution, emulsion or suspension, i.e., in a liquid composition, it can conveniently be sprayed onto the maturing cane plants from a boom-spray, or when it is applied as a dust composition which contains the active compound diluted with an inert solid such as clay it can be dusted on from an aircraft or the like.

In preparing suitable liquid compositions, surface active agents of the type described, for instance, in U.S. Pat. No. 3,224,865, column 2, lines 61-66 or in U.S. Pat. No. 3,245,775, column 2, lines 57-64 are convenient to use. The preferred surfactants for use in liquid compositions of the present invention are those of the non-ionic type, e.g., alkyl phenoxy poly(ethenoxy)ethanols such as adducts of nonylphenol and ethylene oxide; trimethyl nonyl polyethylene glycol ethers; polyethylene oxide adducts of fatty and resin acids, and long chain alkyl mercaptan adducts with ethylene oxide.

With the type of boom-spray apparatus used in this work, it has been found convenient to apply the active ripener to the sugarcane field in the form of an aqueous solution, suspension or emulsion having a concentration of active agent such that the application at the rate of from 5 to 20 gallons per acre (about 50 to 200 liters per hectare) of liquid composition will provide the required dosage of active chemical. However, the use of lower or higher gallonages may be preferred when a different dispensing mechanism is used.

The preferred carrier for the active ripening agent is water to which about 0.1 to 2% by weight of surface active agent has been added. However, instead of using water as the carrier, non-phytotoxic mineral oils either as such or in the form of water-in-oil or oil-in-water-emulsions may be used similarly in accordance with practices which are otherwise well known in the art of treating vegetation in the field with beneficial growth control agents. Excellent results are obtained when the ripening agents of the present invention constitute essentially the sole active ingredients in the treating composition, but they may also be applied in combination with other agents.

The nature, scope, utility, mode of application and effectiveness of the present invention have been described and exemplified in the foregoing specification. However, these examples are not intended to be limiting. The true scope of the present invention which is entitled to patent protection is particularly pointed out in the appended claims.

What is claimed is:

1. (Replaces claim 7) A compound according to the formula

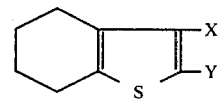

wherein X is cyano or $C_1$–$C_4$ carboalkoxy and Y is (chlorophenyl)ureido, (fluorophenyl) ureido, (trifluoromethylphenyl) ureido, (trifluoromethylchlorophenyl) ureido, (methylmethoxyphenyl) ureido or (chlorodimethoxyphenyl) thioureido.

2. A compound according to claim 1 wherein X is carboethoxy and Y is (4-fluorophenyl)ureido.

3. A compound according to claim 1 wherein Y is (3-chlorophenyl)ureido.

4. A compound according to claim 1 wherein Y is (3-trifluoromethylphenyl)ureido.

5. A compound according to claim 1 wherein Y is (2-chloro-5-trifluoromethylphenyl)ureido.

6. A compound according to claim 1 wherein Y is (2-methoxy-5-methylphenyl)ureido.

7. A compound according to claim 1 wherein Y is chlorophenylureido.

8. 2-(Chloro-2,4-dimethoxyphenyl)-thioureido-3-cyano-4,5-tetramethylenethiophene.

* * * * *